(12) United States Patent
Horisaka et al.

(10) Patent No.: US 7,986,205 B2
(45) Date of Patent: Jul. 26, 2011

(54) MAGNETIC FIELD CONTROL METHOD AND MAGNETIC FIELD GENERATOR

(75) Inventors: Kentarou Horisaka, Nagoya (JP); Hisato Amano, Ibaraki (JP)

(73) Assignee: Hitachi Metals. Ltd, Tokyo (JP)

( * ) Notice: Subject to any disclaimer, the term of this patent is extended or adjusted under 35 U.S.C. 154(b) by 453 days.

(21) Appl. No.: 11/992,778

(22) PCT Filed: Sep. 29, 2006

(86) PCT No.: PCT/JP2006/319485
§ 371 (c)(1),
(2), (4) Date: May 22, 2008

(87) PCT Pub. No.: WO2007/037380
PCT Pub. Date: Apr. 5, 2007

(65) Prior Publication Data
US 2009/0231073 A1    Sep. 17, 2009

(30) Foreign Application Priority Data
Sep. 30, 2005   (JP) .................................. 2005-287756

(51) Int. Cl.
*H01F 1/00*     (2006.01)
*H01F 3/00*     (2006.01)
*H01F 7/00*     (2006.01)
*H01F 7/02*     (2006.01)
*G01V 3/00*     (2006.01)

(52) U.S. Cl. ........ 335/296; 335/301; 335/302; 335/303; 335/306; 335/284; 324/319

(58) Field of Classification Search .................. 335/216, 335/219, 284, 296–306; 324/318, 319, 320; 600/411, 146, 407, 410, 421, 422, 427; 310/152; 336/110, 218
See application file for complete search history.

(56) References Cited

U.S. PATENT DOCUMENTS

| 4,672,346 | A | * | 6/1987 | Miyamoto et al. | ............ 335/296 |
| 4,862,128 | A |   | 8/1989 | Leupold         | ........................ 335/306 |
| 5,099,217 | A | * | 3/1992 | Leupold         | ........................ 335/306 |
| 5,528,212 | A | * | 6/1996 | Challenger et al. | ........... 335/298 |

(Continued)

FOREIGN PATENT DOCUMENTS
EP    0 927 889 A2    7/1999
(Continued)

OTHER PUBLICATIONS

Supplementary European Search Report dated Apr. 20, 2010.

*Primary Examiner* — Anh T Mai
*Assistant Examiner* — Mohamad A Musleh
(74) *Attorney, Agent, or Firm* — Kratz, Quintos & Hanson, LLP

(57) ABSTRACT

There is provided a magnetic field generator 10 which is capable of varying an orientation of a magnetic field at a target position P easily in all directions. The magnetic field generator 10 includes a pair of magnetic field generating units 16a, 16b which are disposed coaxially so that their respective first main surfaces 28a, 28b oppose in parallel to each other, with a gap G in between. The magnetic field generating units 16a, 16b are rotated by rotation drive units 20a, 20b respectively in Arrow A directions. By rotating each of the magnetic field generating units 16a, 16b in the same one direction of the Arrow A directions by the same angle, the orientation of the magnetic field at the target position P is varied on an X-Z plane. On the other hand, by rotating at least one of the magnetic field generating units 16a, 16b in an Arrow A direction so as to change positional relationship between the magnetic pole of the field generating unit 16a and the magnetic pole of the magnetic field generating unit 16b, the inclination of the orientation of the magnetic field at the target position P with respect to the X-Z plane is varied.

9 Claims, 12 Drawing Sheets

U.S. PATENT DOCUMENTS

| | | | |
|---|---|---|---|
| 5,565,834 A * | 10/1996 | Hanley et al. | 335/296 |
| 6,011,396 A * | 1/2000 | Eckels et al. | 324/319 |
| 6,208,142 B1 * | 3/2001 | Wagshul | 324/319 |
| 6,411,187 B1 | 6/2002 | Rotem et al. | 335/296 |
| 6,630,879 B1 * | 10/2003 | Creighton et al. | 335/306 |
| 7,667,462 B2 * | 2/2010 | Song et al. | 324/319 |
| 7,693,570 B2 * | 4/2010 | Green et al. | 600/415 |
| 7,706,858 B1 * | 4/2010 | Green et al. | 600/415 |
| 7,719,396 B2 * | 5/2010 | Umeda et al. | 335/296 |
| 2002/0011844 A1 * | 1/2002 | Biglieri et al. | 324/318 |
| 2004/0249262 A1 | 12/2004 | Werp et al. | |
| 2005/0187424 A1 | 8/2005 | Hambuchen et al. | |
| 2006/0114088 A1 * | 6/2006 | Shachar | 335/219 |

FOREIGN PATENT DOCUMENTS

| | | |
|---|---|---|
| EP | 1 547 540 A1 | 6/2005 |
| JP | 9-90009 | 4/1997 |
| JP | 2002-233575 | 8/2002 |
| JP | 2002-528237 | 9/2002 |
| JP | 2002-536037 | 10/2002 |
| JP | 2003-260026 | 9/2003 |
| JP | 2005-103091 | 4/2005 |
| JP | 2005-161052 | 6/2005 |
| WO | WO 00/25864 A1 | 5/2000 |
| WO | WO 00/45692 A3 | 8/2000 |
| WO | WO 02/34131 A1 | 5/2002 |

* cited by examiner

FIG. 9
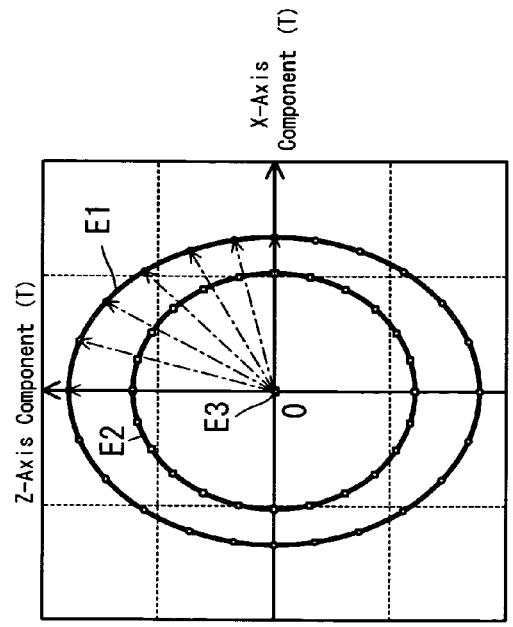
(a)
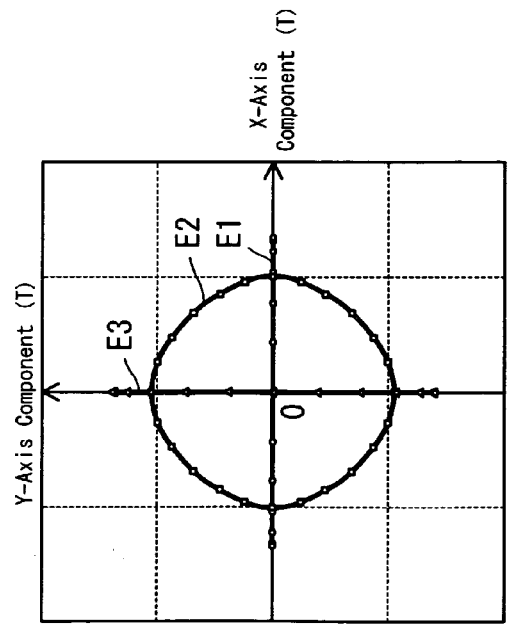
(b)
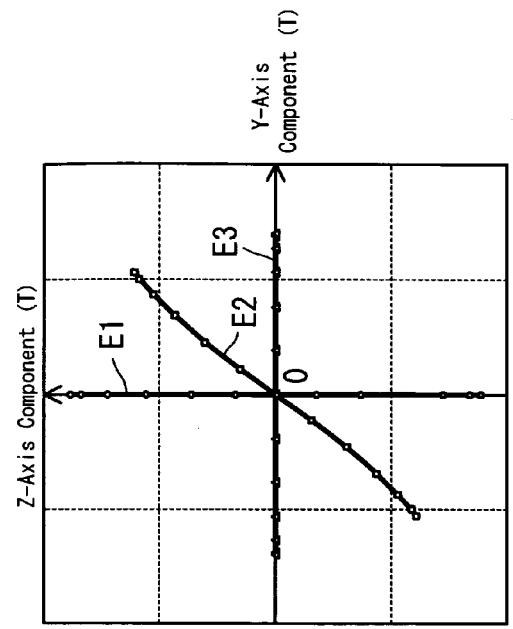
(c)

MAGNETIC FIELD CONTROL METHOD AND MAGNETIC FIELD GENERATOR

FIELD OF THE INVENTION

The present invention relates to a magnetic field control method and a magnetic field generator, and more specifically, to a magnetic field control method and a magnetic field generator in which an orientation of a magnetic field at a target position is changed to an arbitrary direction.

BACKGROUND ART

Conventionally, magnetic field generators in which an orientation of a magnetic field at a target position is variable are public. The applicant of the present invention proposed one in Patent Document 1. According to the magnetic field generator disclosed in Patent Document 1, a magnetic field generating unit of a large diameter and a magnetic field generating unit of a small diameter housed therein are rotated circumferentially, whereby the orientation of a magnetic field which is provided at a target position within the small-diameter magnetic field generating unit is varied on a radial plane.

Meanwhile, in recent years, there have been developments in the field of medical care for medical instrument systems which guide, by working of a magnetic field, an object such as a catheter and a capsule endoscope to an arbitrary position inside the body of a patient. In order to guide an object to an arbitrary position, it is necessary to be able to vary the orientation of the magnetic field at the target position in all directions (any direction). Therefore, the magnetic field generator according to Patent Document 1 which varies the orientation of the magnetic field on a predetermined plane is not applicable to such medical systems. For this reason, these medical systems make use of magnetic field generators such as one disclosed in Patent Document 2 for example. The magnetic field generator disclosed in Patent Document 2 is capable of varying the orientation of the magnetic field at a target position in all directions by circumferential rotation of one magnetic field generating unit and radial travel of the same one magnetic field generating unit.

Patent Document 1: JP-A Hei 9-90009
Patent Document 2: JP-A 2002-536037

DISCLOSURE OF THE INVENTION

Problems to be Solved by the Invention

However, the magnetic field generator according to Patent Document 2 requires means for rotating the magnetic field generating units in the circumferential directions and means for moving the magnetic field generating units in the radial directions. Because of this, there has been a problem of complicated composition of the apparatus as well as a problem of complicated control of the apparatus.

Therefore, a primary object of the present invention is to provide a magnetic field control method and a magnetic field generator in which the orientation of the magnetic field at a target position can be varied easily in all directions.

Means for Solving the Problems

According to an aspect of the present invention, there is provided a magnetic field control method using a pair of coaxially disposed magnetic field generating units each having a first main surface opposed in parallel to the other with a gap and formed with a plurality of magnetic poles, for controlling a magnetic field generated by the pair of magnetic field generating units, sandwiched by the pair of magnetic field generating units and being at a target position on a predetermined plane which is in parallel to the first main surface. The method includes a step of changing an orientation of the magnetic field at the target position on the predetermined plane by rotating each of the magnetic field generating units in a same one direction of circumferential directions by a same angle, and a step of changing an inclination of the orientation of the magnetic field at the target position with respect to the predetermined plane by rotating at least one of the magnetic field generation units in the pair in a circumferential direction so as to change a positional relationship between the magnetic pole in one of the magnetic field generating units and the magnetic pole in the other of the magnetic field generating units.

According to another aspect of the present invention, there is provided a magnetic field generator which includes a pair of coaxially disposed magnetic field generating units each having a first main surface opposed in parallel to the other with a gap and formed with a plurality of magnetic poles; and rotating means for rotating each of the magnetic field generating units in the pair in a circumferential direction for changing an orientation of a magnetic field generated by the pair of magnetic field generating units, sandwiched by the pair of magnetic field generating units and being at a target position on a predetermined plane which is in parallel to the first main surface.

According to the present invention, the orientation of the magnetic field at a target position is varied on the predetermined plane in 360 degrees by rotating each of the magnetic field generating units in the pair in the same circumferential direction by the same angle. Also, by rotating at least one of the magnetic field generating units in the pair in a circumferential direction so as to change a positional relationship between the magnetic pole in one of the magnetic field generating units and the magnetic pole in the other, a change is made to a ratio of the opposed like poles (unlike poles) in the first main surface of one magnetic field generating unit and in the first main surface of the other magnetic field generating unit. By this operation, the orientation of the magnetic field at a target position is tilted with respect to a predetermined plane within a 90 degree range toward the first main surface of one magnetic field generating unit or toward the first main surface of the other magnetic field generating unit. In other words, the orientation of the magnetic field at the target position with respect to the predetermined plane is varied within a range of ±90 degrees. Therefore, by combining rotation of the pair of magnetic field generating units in the same direction by the same angle, and rotation of at least one of the magnetic field generating units in the pair, it is possible to change the orientation of the magnetic field at the target position easily and in all directions. As described, since the orientation of the magnetic field at a target position can be changed easily and in all directions by simply rotating the magnetic field generating units, it is possible to make the composition of the generator simple and it is easy to control the generator.

It should be noted here that a "target position" is a place in a magnetic field which is generated by a pair of magnetic field generating unit, where the orientation and the intensity of the magnetic field is to be controlled.

Preferably, the magnetic field control method further includes a step of changing an intensity of the magnetic field at the target position while maintaining the orientation of the magnetic field at the target position, by changing a relative positional relationship between the pair of magnetic field generating units and the target position. In this case, it is possible to maintain a constant magnetic field intensity at the target position regardless of the orientation of the magnetic field at the target position. In a medical care system where an object which is placed in the body of a patient is guided by working of a magnetic field, it is preferable to maintain the magnetic field intensity which works on the object at a constant level, in addition to varying the orientation of the magnetic field arbitrary. The present invention makes it possible to keep a constant magnetic field intensity at a target position, and therefore is utilized suitably in a medical care system where an object is guided by working of a magnetic field. The relative positional relationship between the pair of magnetic field generating units and the target position is changed, for example, by moving each of the magnetic field generating units in the pair in the same direction in parallel to the predetermined plane, by the same distance.

It is preferable also, that at least one of the magnetic field generating units has a second main surface which faces away from the first main surface, and the second main surface is provided with a magnetic body. In this case, it is possible to reduce magnetic flux leakage toward the second main surface, and to increase magnetic field intensity at a target position.

Further, it is preferable that the first main surface in at least one of the magnetic field generating units has a circular outer shape. In this case, the area of mutually opposed regions in the first main surface of one magnetic field generating unit and in the first main surface of the other magnetic field generating unit does not change when, for example, one of the magnetic field generating units in the pair is rotated. Because there is no decrease in the area where the first main surfaces of the magnetic field generating units in the pair oppose to each other, it is possible to make effective use of the magnetic flux from the magnetic field generating units.

In the first main surface of the magnetic field generating unit, magnetic flux makes short cuts from the positive pole (N pole) to the negative pole (S pole) near pole-to-pole regions where unlike poles are located closely to each other. For this reason, more magnetic flux makes short cuts in the first main surface as there are more magnetic poles formed in the first main surface, resulting in a decrease in the amount of magnetic flux which works on the target position. Preferably, the first main surface in at least one of the magnetic field generating units is formed with two of the magnetic poles. By making the number of magnetic poles in the first main surface in the magnetic field generating unit as few as possible as described, it becomes possible to reduce the amount of magnetic flux which makes short cuts in the first main surface. This arrangement allows the magnetic flux to work efficiently at a target position, and to increase the magnetic field intensity at the target position.

Further preferably, at least one of the magnetic field generating units is provided by a single permanent magnet. In this case, it is possible to reduce the number of parts in the magnetic field generating unit, and it becomes possible to compose the generator more simply.

Further, preferably, at least one of the magnetic field generating units is constituted by a plurality of permanent magnets and a holding member which holds the permanent magnets. In this case, the magnetic field generating unit can be obtained easily by holding individual permanent magnets which are magnetized separately from each other, by using a holding member. Also, it becomes possible to dispose the permanent magnets at a space from each other, i.e., it becomes possible to separate unlike poles from each other in the first main surface. In other words, it becomes possible to eliminate permanent magnets from near pole-to-pole regions which have virtually no effects on the target position. By reducing the amount of permanent magnet to be used, it becomes possible to reduce the weight of the magnetic field generating units, and to reduce the weight of the magnetic field generator.

The above-described object, other objects, characteristics, aspects and advantages of the present invention will become clearer from the following detailed description of embodiments to be made with reference to the attached drawings.

BRIEF DESCRIPTION OF THE DRAWINGS

FIG. 9 is a set of diagrams which show magnetic field intensity changes at a target position associating with changes in the orientation of the magnetic field at the target position: FIG. 9(a) shows the magnetic field intensity changes at the target position using X-axis component and Z-axis component; FIG. 9(b) shows the magnetic field intensity changes at the target position using X-axis component and Y-axis component; and FIG. 9(c) shows the magnetic field intensity changes at the target position using Y-axis component and Z-axis component.

LEGEND

10 Magnetic field generator
16$a$, 16$b$, 100, 108, 114 Magnetic field generating units
20$a$, 20$b$ Rotation drive units
28$a$, 28$b$, 106, 110, 116 First main surfaces 26a, 26b Magnetic bodies
30a, 30b, 112, 118 Second main surfaces
34a, 34b Sliders
102a, 102b Permanent magnets
104 Holding member
G Gap
P Target position

BEST MODE FOR CARRYING OUT THE INVENTION

Hereinafter, embodiments of the present invention will be described with reference to the drawings.

Figure 1:
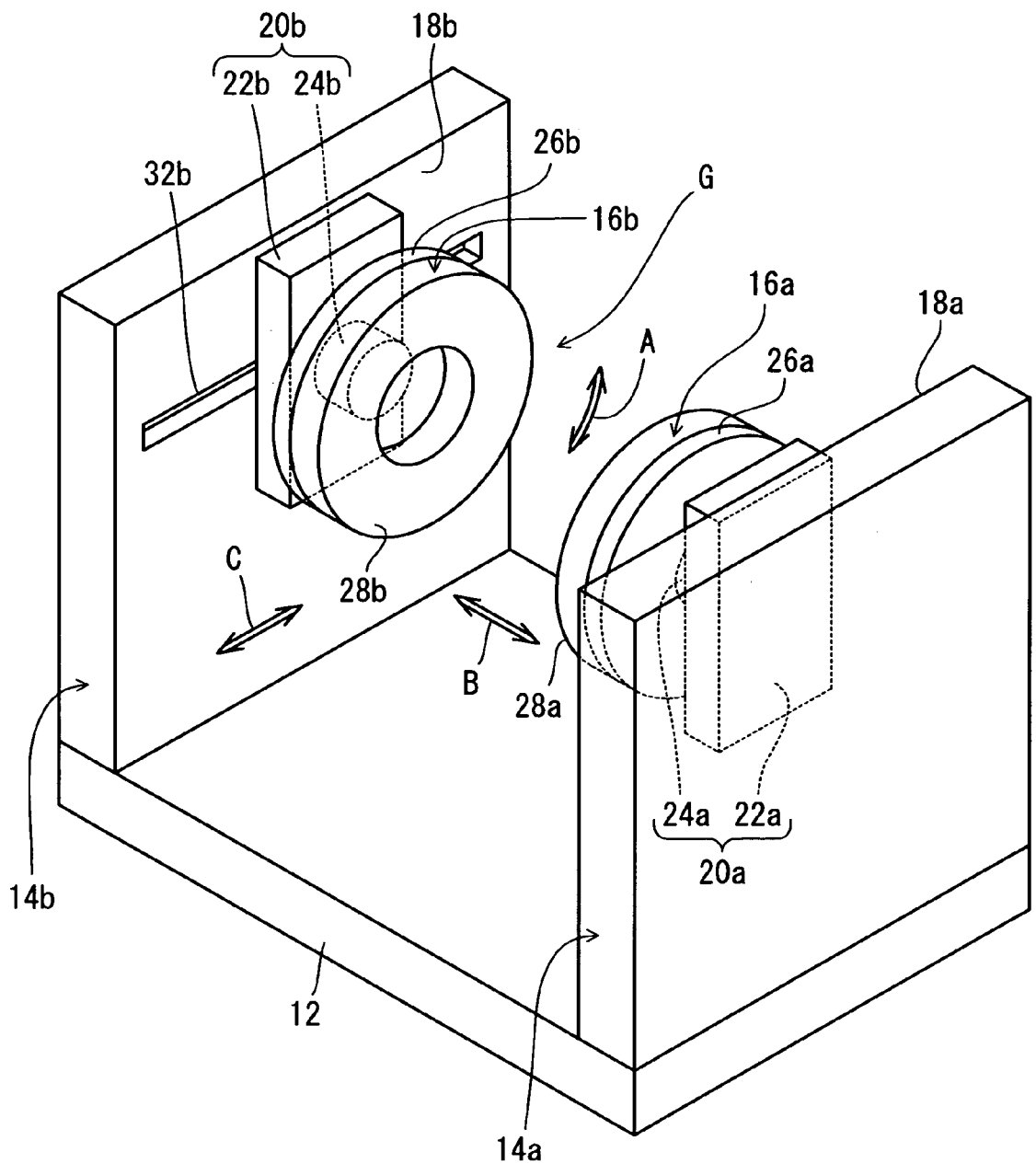
FIG. 1 is a diagram showing a perspective view of a magnetic field generator according to an embodiment of the present invention.
Figure 2:
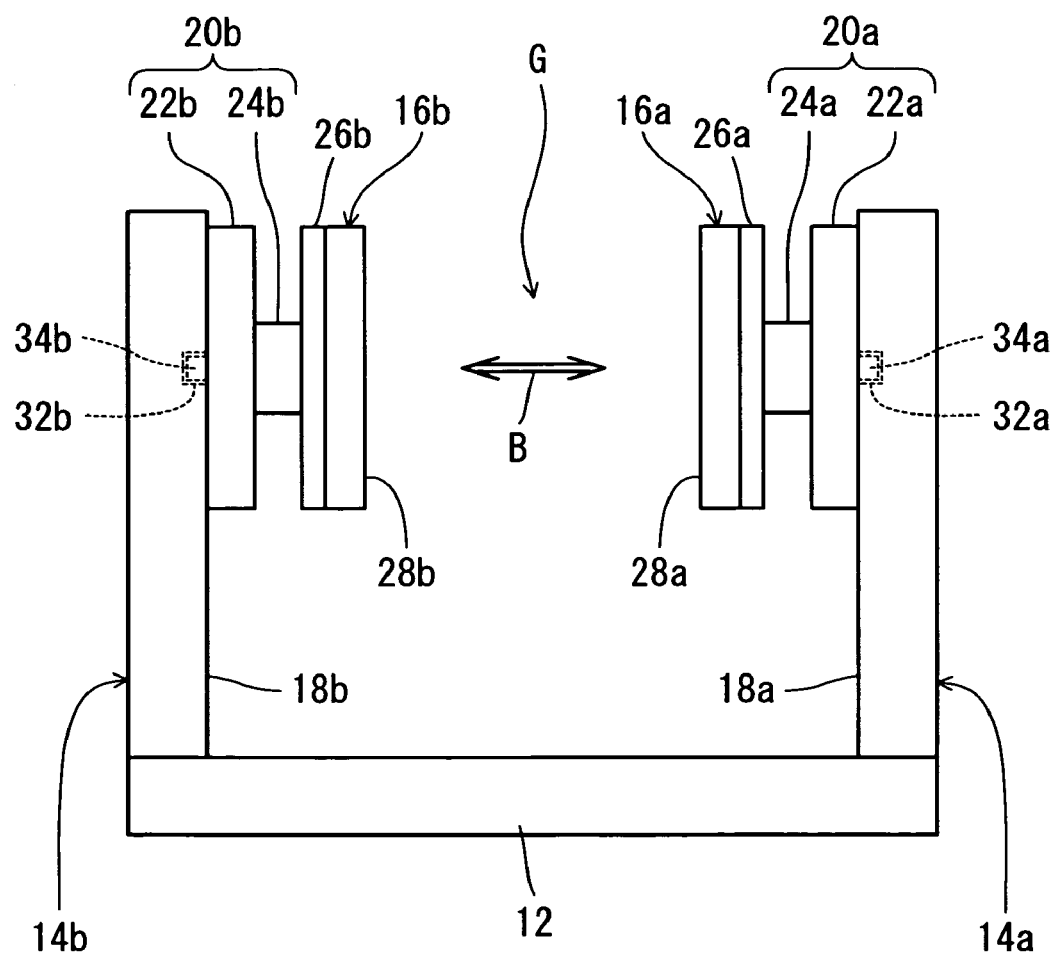
FIG. 2 is a diagram showing a front view of the magnetic field generator in FIG. 1.

Referring to FIG. 1 and FIG. 2, a magnetic field generator 10 according to an embodiment of the present invention includes a mount 12, a pair of supports 14a, 14b and a pair of magnetic field generating units 16a, 16b.

The supports 14a, 14b are opposed to each other on an upper surface of the mount 12. On an opposing surface 18a of the support 14a, there is provided a rotation drive unit 20a for rotating the magnetic field generating unit 16a in circumferential directions (Arrow A directions). Likewise, on an opposing surface 18b of the support 14b, there is provided a rotation drive unit 20b for rotating the magnetic field generating unit 16b in the Arrow A directions.

The rotation drive unit 20a includes a main body 22a and a rotation member 24a. The magnetic field generating unit 16a is attached to the rotation member 24a via a magnetic body 26a. Likewise, the rotation drive unit 20b includes a main body 22b and a rotation member 24b. The magnetic field generating unit 16b is attached to the rotation member 24b via a magnetic body 26b. The magnetic field generating units 16a, 16b attached to the rotation drive units 20a, 20b as described above are disposed coaxially so that their first main surfaces 28a, 28b face in parallel to each other with a gap G in between.

Here, reference will be made to FIG. 3 and FIG. 4, to provide detailed description of the magnetic field generating units 16a, 16b, each of which generates a magnetic field. Here, the description will cover the magnetic field generating unit 16a. Since the magnetic field generating units 16a, 16b have the same construction, the magnetic field generating unit 16b will be readily understood from the description of the other by reading with simple substitution of the reference symbol "a" with "b", so no separate description will be given.

Figure 3:
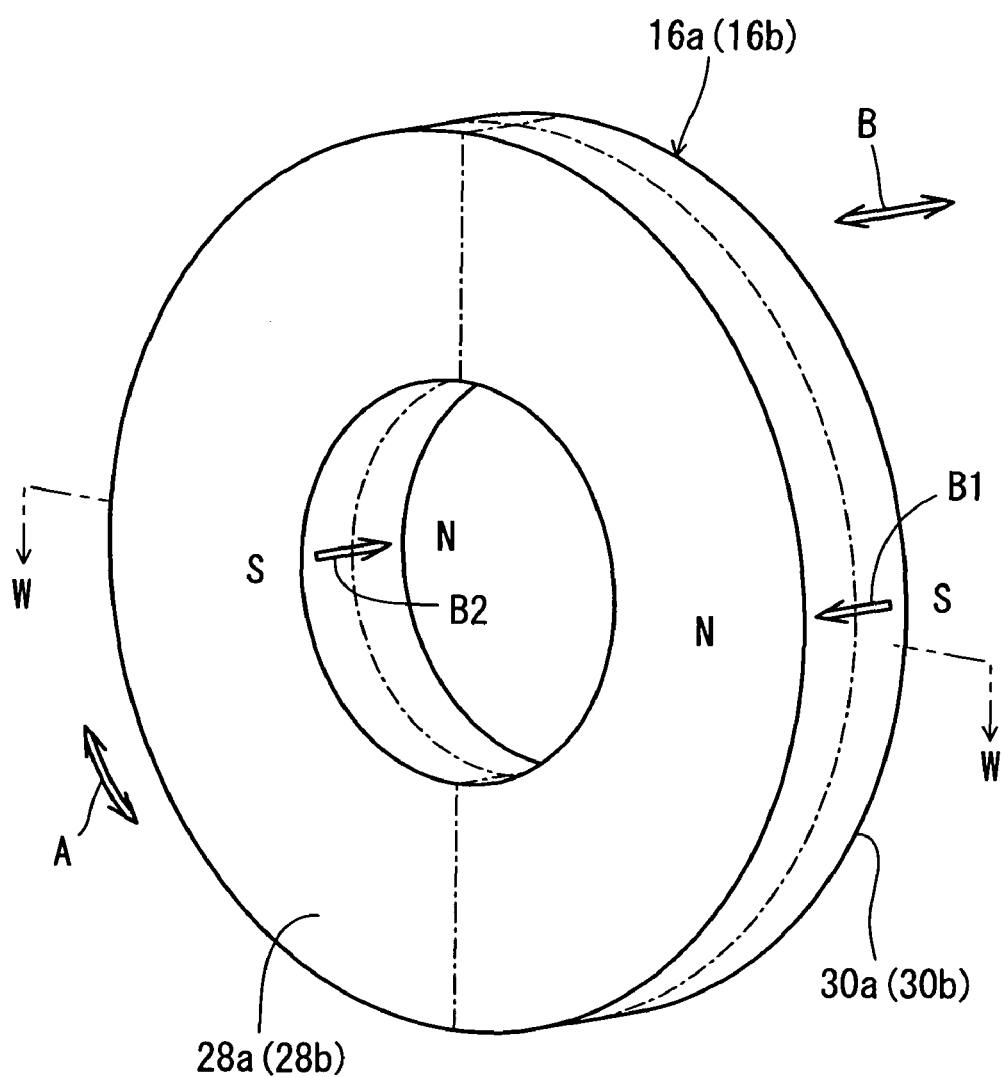
FIG. 3 is a diagram showing a perspective view of a magnetic field generating unit.

As shown in FIG. 3, the magnetic field generating unit 16a is formed like a disc (ring) which has a center with a through-hole in extending in axial directions (Arrow B directions: See FIG. 2), so the magnetic field generating unit 16a has an annular first main surface 28a and an annular second main surface 30a. Therefore, the first main surface 28a and the second main surface 30a have a circular outer shape.

The magnetic field generating unit 16a is made of a single permanent magnet. A half of the magnetic field generating unit 16a is magnetized (given a polarity) in one direction (hereinafter Arrow B1 direction) of the Arrow B directions while the remaining half of the magnetic field generating unit 16a is magnetized in the other direction (hereinafter Arrow B2 direction) of the Arrow B directions. Therefore, the first main surface 28a is formed with an S pole and an N pole. On the other hand, the second main surface 30a is formed with an N pole at a location corresponding to the S pole in the first main surface 28a, and an S pole at a location corresponding to the N pole in the first main surface 28a.

Figure 4:
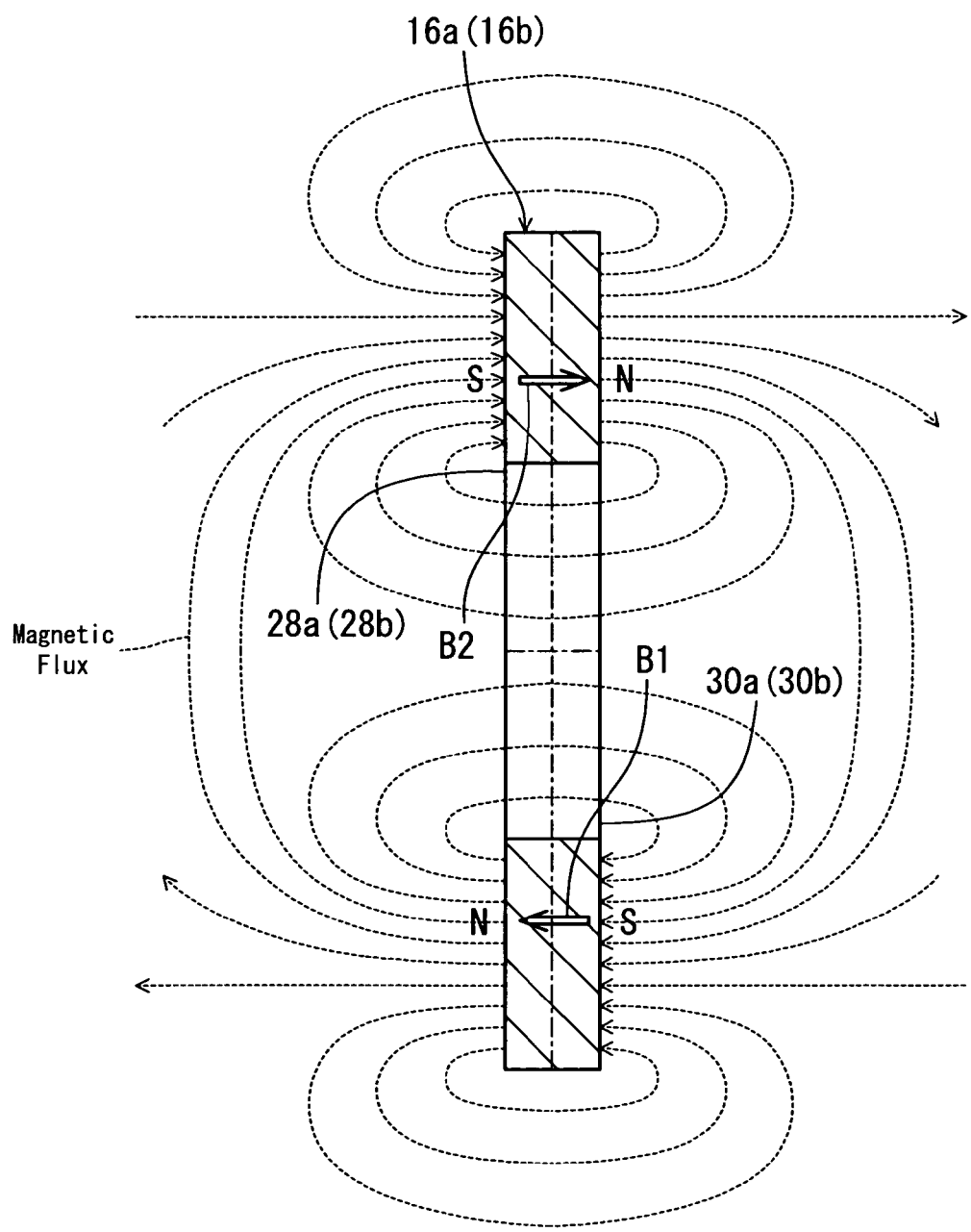
FIG. 4 is a diagram showing a sectional view of the magnetic field generating unit taken in lines W-W (FIG. 3).

FIG. 4 shows a magnetic flux distribution in the magnetic field generating unit 16a which is of a so-called two-face-dual-polarity design. FIG. 4 shows a magnetic flux distribution in a W-W section (See FIG. 3) of the magnetic field generating unit 16a. As shown in FIG. 4, magnetic flux which comes out of a center area of the N pole in the first main surface 28a goes beyond the through-hole, and enters a center area of the S pole in the first main surface 28a. On the other hand, magnetic flux which comes out of an inner circumferential edge area of the N pole in the first main surface 28a goes through the through-hole, and enters an inner circumferential edge area of the S pole in the second main surface 30a. Further, magnetic flux which comes out of an outer circumferential edge area of the N pole in the first main surface 28a goes beyond the outer circumferential surface, and enters an outer circumferential edge area of the S pole in the second main surface 30a. Likewise, magnetic flux which comes out of the N pole in the second main surface 30a enters the S pole in the second main surface 30a and the S pole in the first main surface 28a.

Returning to FIG. 1 and FIG. 2, the rotation drive unit 20a has, in its main body 22a, an unillustrated motor which rotates the rotation member 24a in the circumferential directions (Arrow A directions), and thereby rotates the magnetic field generating unit 16a in Arrow A directions. Likewise, the rotation drive unit 20b has, in its main body 22b, an unillustrated motor which rotates the rotation member 24b in Arrow A directions, and thereby rotates the magnetic field generating unit 16b in Arrow A directions. The operation of the rotation drive units 20a, 20b as described is controlled by an unillustrated controller. In other words, the controller that defines control means controls the direction of rotation and the angle of rotation of the magnetic field generating units 16a, 16b. In the present embodiment, rotating means is defined by the rotation drive units 20a, 20b, each of which includes a motor that defines driving means.

The magnetic body 26a, which is provided on the second main surface 30a of the magnetic field generating unit 16a, is formed like a disc which has the same diameter as the magnetic field generating unit 16a. The magnetic field generating unit 16a and the magnetic body 26a are bonded to each other so their outer circumferential surfaces are flush with each other. Likewise, the magnetic body 26b, which is provided on the second main surface 30b of the magnetic field generating unit 16b, is formed like a disc which has the same diameter as the magnetic field generating unit 16b. The magnetic field generating unit 16b and the magnetic body 26b are bonded to each other so their outer circumferential surfaces are flush with each other.

As shown in FIG. 2, the opposing surface 18a of the support 14a is formed with a groove 32a which extends in fore-and-aft directions (Arrow C directions: See FIG. 1). Inside the groove 32a, there is provided a slider 34a to which the main body 22a of the rotation drive unit 20a is attached. Likewise, the opposing surface 18b of the support 14b is formed with a groove 32b which extends in the Arrow C directions. Inside the groove 32b, there is provided a slider 34b to which the main body 22b of the rotation drive unit 20b is attached.

The slider 34a is moved in the Arrow C directions by an unillustrated actuator provided in the support 14a, and thereby moves the rotation drive unit 20a and the magnetic field generating unit 16a in the Arrow C directions. Likewise, the slider 34b is moved in the Arrow C directions by an unillustrated actuator provided in the support 14b, and thereby moves the rotation drive unit 20b and the magnetic field generating unit 16b in the Arrow C directions. Operation of the actuators for moving the sliders 34a, 34b is controlled by an unillustrated controller. In other words, the controller which defines the control means controls the direction of travel and the distance of travel of the magnetic field generating units 16a, 16b. In the present embodiment, the sliders 34a, 34b and the actuators which define driving means for moving them constitute moving means.

Next, description will cover a magnetic field control method in the magnetic field generator 10 which is constituted as described thus far.

Figure 5:
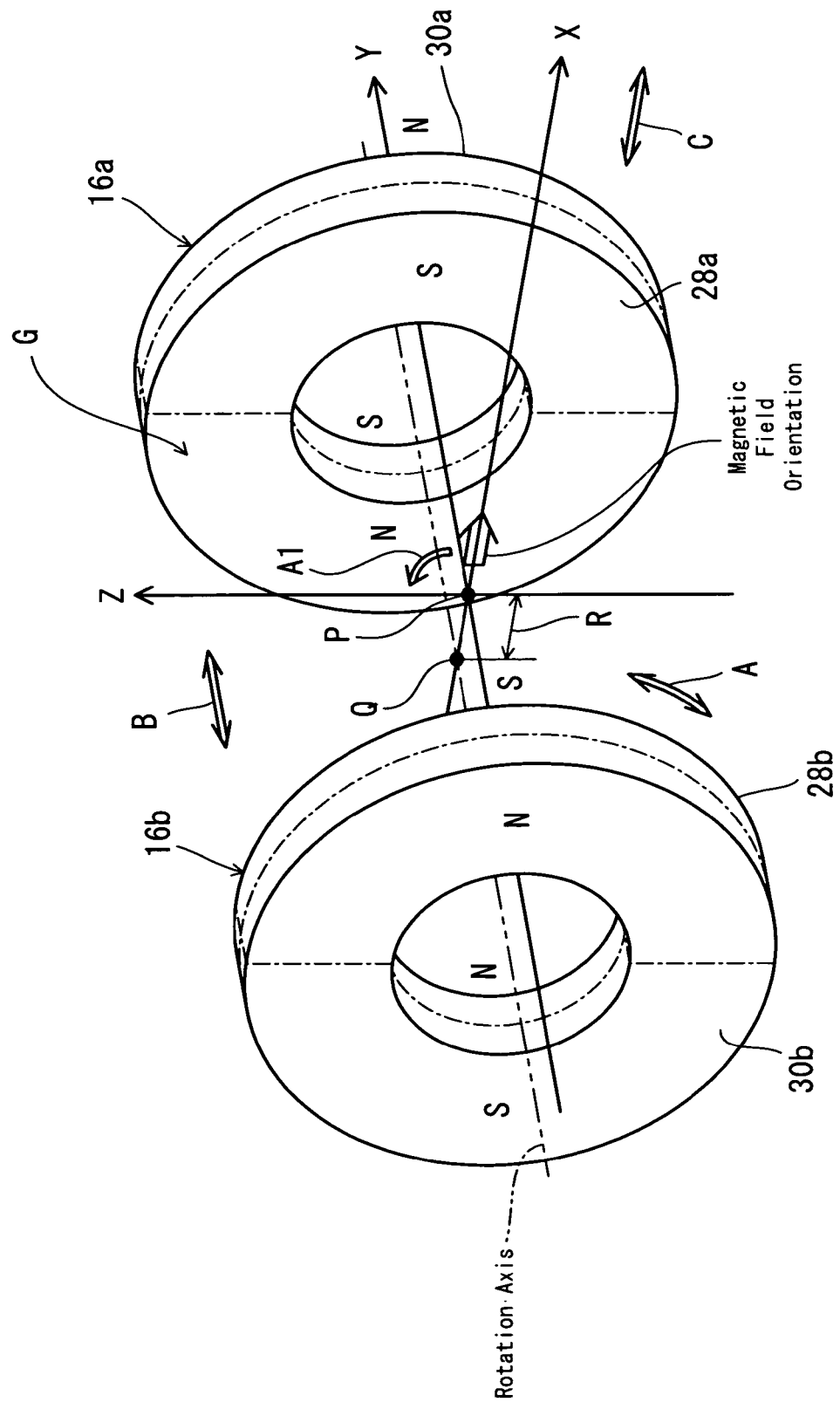
FIG. 5 is a diagram showing a perspective view of a pair of magnetic field generating units facing to each other on their respective first main surfaces, with like poles being opposed to each other in alignment.
Figure 6:
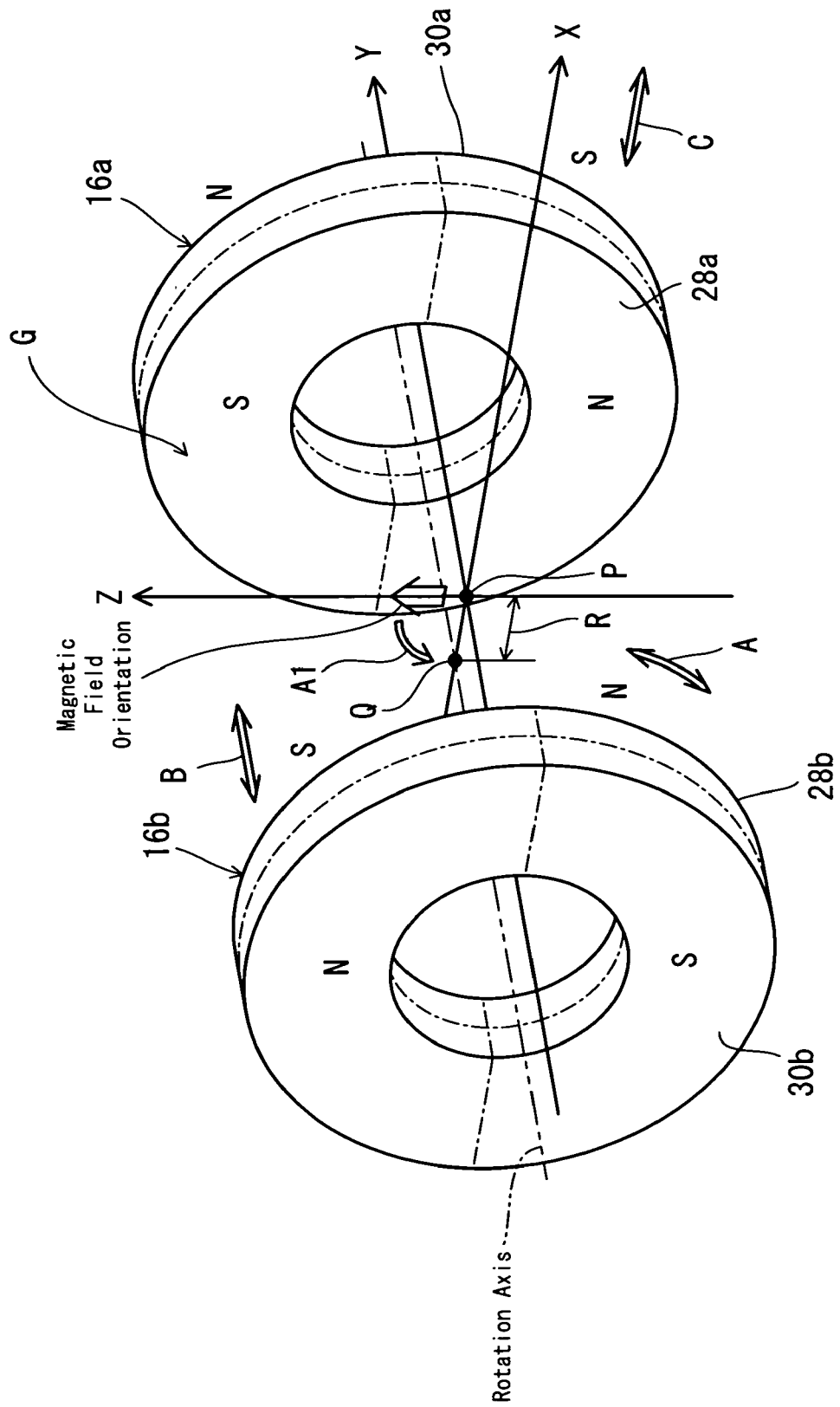
FIG. 6 is a diagram showing a perspective view of a state where each of the magnetic field generating units in the pair was rotated by 90 degrees in the same circumferential direction from the state shown in FIG. 5.
Figure 7:
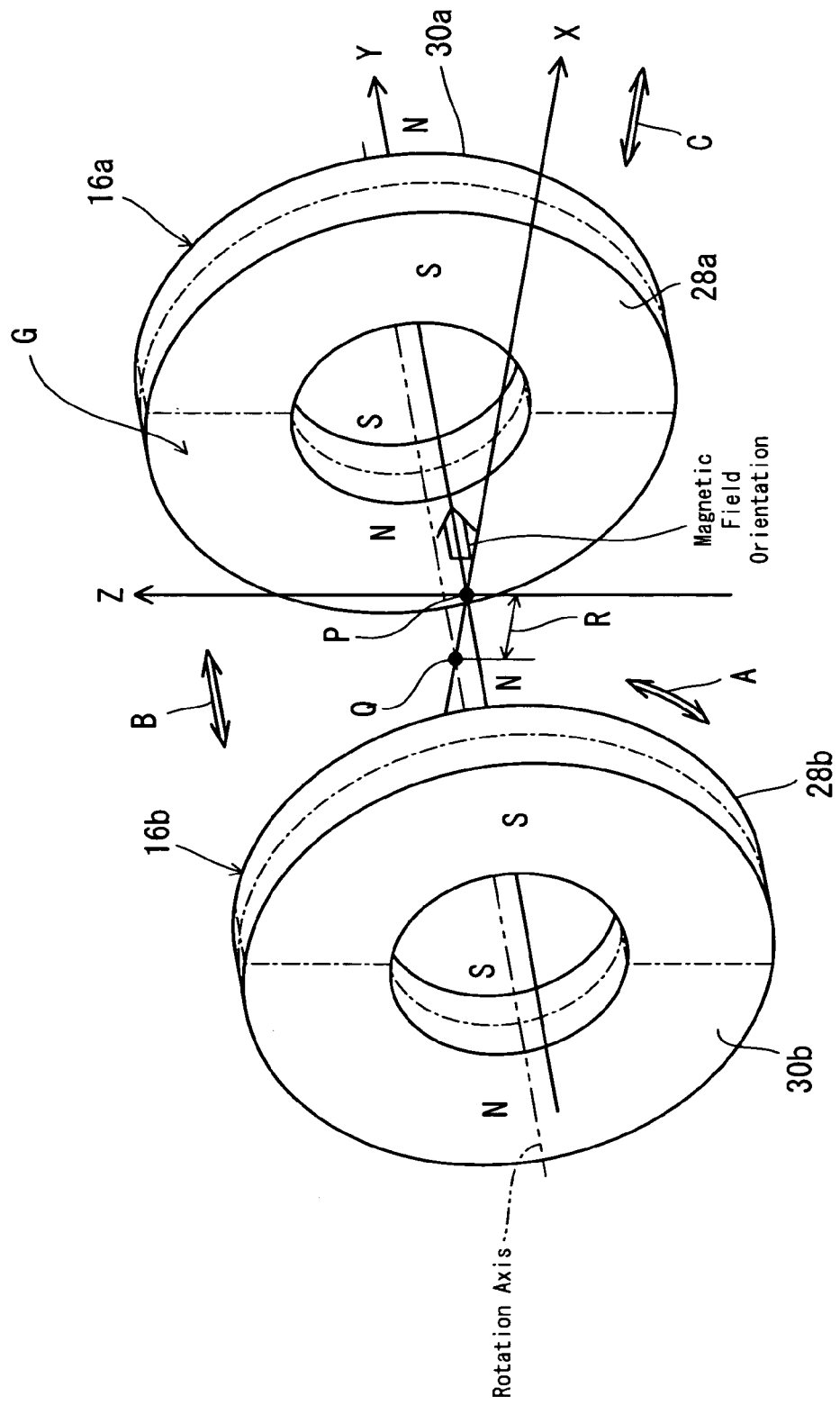
FIG. 7 is a diagram showing a perspective view of the pair of magnetic field generating units facing to each other on their respective first main surfaces, with unlike poles being opposed to each other in alignment.

Referring to FIG. 5 through FIG. 7, in the magnetic field generator 10, the orientation of the magnetic field at a target position P is controlled by rotating the magnetic field generating units 16a, 16b. It should be noted here that FIG. 5 through FIG. 7 show the magnetic field generating units 16a, 16b only.

As shown in FIG. 5, here, assume an axis which is equidistant from the first main surfaces 28a, 28b, extends in Arrow C directions, and is perpendicular to an axis of rotation (indicated by a double-dotted dashed line) of the magnetic field generating units 16a, 16b. This axis is defined as an X axis. Then, assume an axis which extends in Arrow B directions perpendicularly to the X axis, and this axis is defined as a Y axis. Further, an axis which is perpendicular to the X axis and the Y axis is defined as a Z axis. With the above, an intersection made by the X axis, the Y axis and the Z axis is defined as a target position P. In other words, the target position P is an intersection made by an X-Z plane which is sandwiched by the pair of magnetic field generating units 16a, 16b and is parallel to the first main surfaces 28a, 28b; an X-Y plane which is perpendicular to the X-Z plane; and an Y-Z plane which is perpendicular to the X-Z plane and the X-Y plane. In the present embodiment, the X-Z plane defines the predetermined plane. Further, note that on the X axis, the side closer to the viewer than the target position P will be a plus zone while the farther side is defined as a minus zone. On the Y axis, the right side of the target position P (the side closer to the magnetic field generating unit 16a) is defined as a plus zone while the left side (the side closer to the magnetic field generating unit 16b) is defined as a minus zone. On the Z axis, the side higher than the target position P is defined as a plus zone while the lower side is defined as a minus zone.

In the magnetic field generator 10, each of the magnetic field generating units 16a, 16b is rotated in the same one direction of the Arrow A directions by the same angle, whereby the orientation of the magnetic field at the target position P is varied on the X-Z plane. Also, at least one of the magnetic field generating units 16a, 16b is rotated in an Arrow A direction so as to change a positional relationship between the magnetic pole of the magnetic field generating unit 16a and the magnetic pole of the magnetic field generating unit 16b, whereby, an inclination of the orientation of the magnetic field with respect to the X-Z plane at the target position P is varied.

Here, the magnetic field generating units 16a, 16b will be rotated from the state shown in FIG. 5 as a home position. In the state shown in FIG. 5, the first main surfaces 28a, 28b have their like poles opposed to each other in alignment (full repellence state). Also in the state shown in FIG. 5, the magnetic field generating units 16a, 16b are disposed so that a distance R, which is from an intersection Q made by the rotation axis (center axis) of the magnetic field generating units 16a, 16b and the X axis to the target position P, is greater than "0". As will be described later, there can be a case where there is no magnetic field at the target position P if the target position P and the intersection Q are located at the same position (in the case where the distance R is "0"), depending upon positional relationship of the magnetic poles in the first main surfaces 28a, 28b. Specifically, there exists no magnetic field at the target position P in the full attraction state shown in FIG. 7. For this reason, the magnetic field generating units 16a, 16b are disposed so that the distance R from the intersection Q to the target position P is greater than "0".

In the state shown in FIG. 5, much of the magnetic flux from the N pole in the first main surface 28a does not proceed to the S pole in the first main surface 28b, but in the Arrow C directions and toward the plus side of the X axis, and then enters the S pole in the first main surface 28a. Likewise, much of the magnetic flux from the N pole in the first main surface 28b does not proceed to the S pole in the first main surface 28a, but in the Arrow C directions and toward the plus side of the X axis, and then enters the S pole in the first main surface 28b. Therefore, the orientation of the magnetic field at the target position P is in the plus direction of the X axis.

First, description will cover a case where the orientation of the magnetic field at the target position P is changed on the X-Z plane. Here, the magnetic field generating units 16a, 16b will be rotated by the same angle, from the state shown in FIG. 5, in a counter clockwise direction (hereinafter Arrow A1 direction) of the Arrow A directions as viewed from the second main surface 30b of the magnetic field generating unit 16b.

As the rotation drive units 20a, 20b (See FIG. 1) rotate their respective magnetic field generating units 16a, 16b in the Arrow A1 direction by the same angle, the orientation of the magnetic flux which passes the target position P rotates in the Arrow A1 direction on the X-Z plane. As a result, the orientation of the magnetic field at the target position P rotates in the Arrow A1 direction on the X-Z plane. Then, as shown in FIG. 6, when each of the magnetic field generating units 16a, 16b has been rotated by 90 degrees, the S poles on the first main surfaces 28a, 28b come on the upper side while the N poles come down on the lower side. Under this state, the orientation of the magnetic field at the target position P is in the plus direction of the Z axis.

As the magnetic field generating units 16a, 16b are rotated further from the state shown in FIG. 6 in the Arrow A1 direction by the same angle, the orientation of the magnetic field at the target position P is changed to the minus direction of the X axis, then to the minus direction of the Z axis, and then back to the plus direction of the X axis, sequentially. In other words, by rotating each of the magnetic field generating units 16a, 16b in the Arrow A1 direction by 360 degrees, the orientation of the magnetic field at the target position P is changed by 360 degrees on the X-Z plane.

It should be noted here that by rotating the magnetic field generating units 16a, 16b in the clockwise direction (reverse direction of the Arrow A1 direction) of the Arrow A directions by the same angle from the state shown in FIG. 5, the orientation of the magnetic field at the target position P is rotated on the X-Z plane, obviously, in the reverse direction of the Arrow A1 direction.

Next, description will cover a case where an inclination of the orientation of the magnetic field at the target position P with respect to the X-Z plane is changed. Here, only the magnetic field generating unit 16b will be rotated in one of the Arrow A directions, from the state shown in FIG. 5.

As the rotation drive unit 20b (See FIG. 1) rotates the magnetic field generating unit 16b in one of the Arrow A directions, positional relationship between the magnetic pole of the field generating unit 16a and the magnetic pole of the magnetic field generating unit 16b is changed. In other words, a ratio of the opposed like poles (unlike poles) in the first main surfaces 28a, 28b is changed. This changes the inclination of the orientation of the magnetic field at the target position P with respect to the X-Z plane. Here, by rotating the magnetic field generating unit 16b in one of the Arrow A directions from the state shown in FIG. 5, a ratio of opposition by the N pole in the first main surface 28b to the S pole in the first main surface 28a increases, and the orientation of the magnetic flux which passes the target position P is tilted toward the first main surface 28a. Therefore, the orientation of the magnetic field at the target position P is tilted from the plus direction of the X axis to the plus direction of the Y axis.

Figure 8:
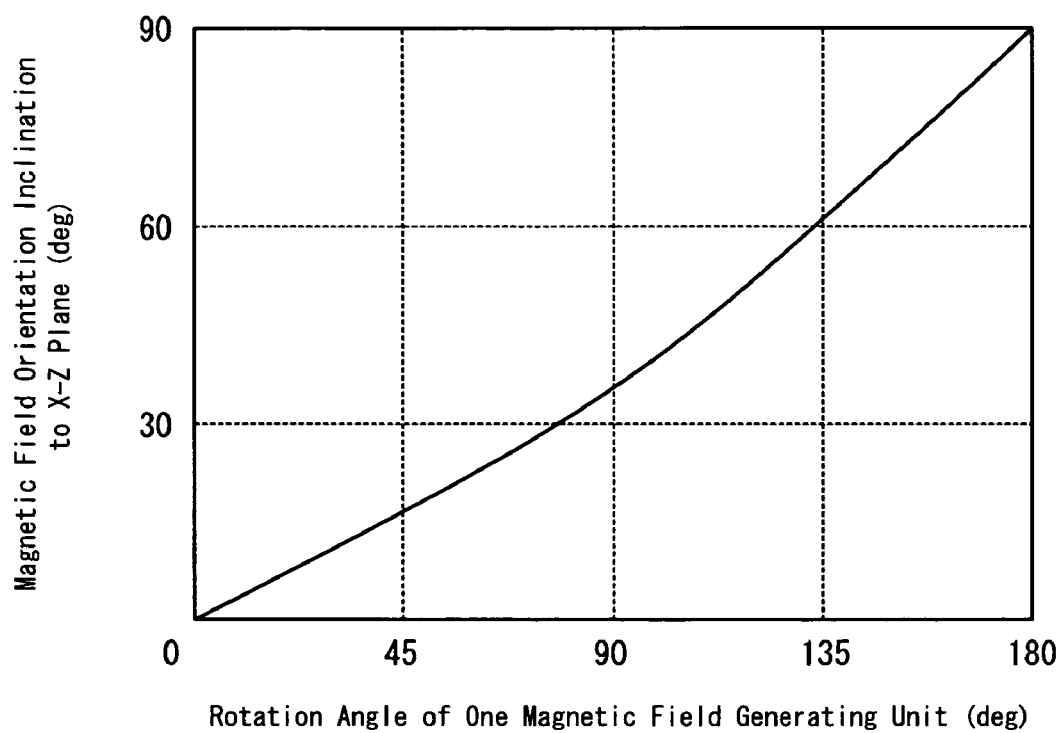
FIG. 8 is a graph which shows a case where only one of the magnetic field generating units is rotated from the state in FIG. 5; the graph shows a relationship between an angle of rotation of the magnetic field generating unit and an angle of inclination of the orientation of the magnetic field at a target position with respect to an X-Z plane.

Referring also to FIG. 8, as the angle of rotation of the magnetic field generating unit 16b increases, the inclination of the orientation of the magnetic field at the target position P with respect to the X-Z plane increases also. Then, as shown in FIG. 7, when the magnetic field generating unit 16b is rotated by 180 degrees, there comes a state where unlike poles in the first main surfaces 28a, 28b oppose to each other in alignment (full attraction state). Under this state, the orientation of the magnetic flux which passes the target position P is in a direction from the first main surface 28b toward the first main surface 28a. Therefore, the orientation of the magnetic field at the target position P is tilted by 90 degrees with respect to the X-Z plane, i.e., in the plus direction of the Y axis.

It should be noted here that rotation of the magnetic field generating unit 16b in whichever direction of the Arrow A directions from the state shown in FIG. 5 will change the orientation of the magnetic field at the predetermined position P accordingly. Further, if the orientation of the magnetic field at the target position P is to be tilted toward the minus direction of the Y axis, magnetic field generating unit 16a should be rotated from the state shown in FIG. 5.

As described, by rotating at least one of the magnetic field generating units 16a, 16b in one of the Arrow A directions so as to change the positional relationship between the magnetic pole of the field generating unit 16a and the magnetic pole of the magnetic field generating unit 16b, it is possible to change the inclination of the orientation of the magnetic field at the target position P with respect to the X-Z plane toward the plus or minus direction of the Y axis. In other words, it is possible to change the inclination of the orientation of the magnetic field at the target position P with respect to the X-Z plane by ±90 degrees.

As described above, according to the magnetic field generator 10, it is possible to change the orientation of the magnetic field at the target position P in all directions (any direction) by combining rotation of the magnetic field generating units 16a, 16b in the same direction by the same angle and rotation of at least one of the magnetic field generating units 16a, 16b.

In the magnetic field generator 10, the controller controls the direction of rotation and the angle of rotation of the magnetic field generating units 16a, 16b according to a necessary change in the orientation of the magnetic field at the target position P. With this arrangement, the orientation of the magnetic field at the target position P can be changed to a desired orientation.

For the sake of reference, under the full attraction state shown in FIG. 7, magnetic flux from the N pole of the first main surface 28a and magnetic flux from the N pole of the first main surface 28b cancel each other almost completely at the intersection Q. As a result, there is almost no magnetic field existing at the intersection Q under the full attraction state. In other words, magnetic field intensity at the intersection Q is almost 0 T under the full attraction state. For this reason, the magnetic field generating units 16a, 16b are disposed so that the distance R from the intersection Q to the target position P will be greater than "0".

As the positional relationship between the target position P and the magnetic poles in the magnetic field generating units 16a, 16b is changed and whereby the orientation of the magnetic field at the target position P is changed, magnetic field intensity at the target position P changes. FIG. 9 shows magnetic field intensity changes at the target position P when the orientation of the magnetic field is changed. FIG. 9(a) shows the magnetic field intensity changes at the target position P using X-axis component and Z-axis component. FIG. 9(b) shows the magnetic field intensity changes at the target position P using X-axis component and Y-axis component, and FIG. 9(c) shows the magnetic field intensity changes at the target position P using Y-axis component and Z-axis component.

Referring to FIG. 9(a) through FIG. 9(c), E1 through E3 show magnetic field intensity changes at the target position P when the magnetic field generating units 16a, 16b are rotated in the same one direction of the Arrow A directions by the same angle. Specifically, E1 shows magnetic field intensity changes when the magnetic field generating units 16a, 16b were rotated while maintaining a full repellence state (the state shown in FIG. 5). E2 shows magnetic field intensity changes when the magnetic field generating units 16a, 16b are rotated in the same direction by the same angle while maintaining a state where one of the magnetic field generating units 16a, 16b was rotated from the state shown in FIG. 5 in one of the Arrow A directions by 90 degrees. In other words, E2 shows magnetic field intensity changes when the magnetic field generating units 16a, 16b are rotated while maintaining a half of the S pole and a half of the N pole in one of the first main surfaces 28a, 28b opposed to a half of the S pole and a half of the N pole in the other (half-repellence-half-attraction state). E3 shows magnetic field intensity changes when the magnetic field generating units 16a, 16b were rotated while maintaining a full attraction state (the state shown in FIG. 7).

From FIG. 9(a) through FIG. 9(c), it is possible to see X-axis component, Y-axis component and Z-axis component of the magnetic field intensity at the target position P when the magnetic field at the target position P has a given orientation. For example, see a plurality of arrows (indicated by dashed lines) in FIG. 9(a), each extending from the point of origin to a point on E1: The orientation of the arrow indicates the orientation of the magnetic field at the target position P on the X-Z plane, whereas the length of the arrow indicates the magnetic field intensity at the target position P. The arrow increases in its length as the orientation of the magnetic field at the target position P is changed from the plus direction of the X axis to the plus direction of the Z axis. As described, it is possible to read from E1 that the magnetic field intensity at the target position P increases as the orientation of the magnetic field at the target position P is changed from the plus direction of the X axis to the plus direction of the Z axis.

Observing E1 in FIG. 9(a) through FIG. 9(c), it is understood that when the magnetic field generating units 16a, 16b are rotated while maintaining a full repellence state, the orientation of the magnetic field at the target position P is not changed to Y-axial directions, and the magnetic field intensity does not have a Y-axis component. Therefore, it is understood from E1 in FIG. 9(a) through FIG. 9(c), that rotating the magnetic field generating units 16a, 16b while maintaining a full repellence state will change only the X-axis component and the Z-axis component in the magnetic field intensity as the orientation of the magnetic field at the target position P changes.

Likewise, observing E2 in FIG. 9(a) through FIG. 9(c), it is understood that when the magnetic field generating units 16a, 16b are rotated while maintaining a half-repellence-half-attraction state, the magnetic field intensity at the target position P has a component in each of the X axial direction, Y axial direction and Z axial direction. In other words, it is understood that each directional component of the magnetic field intensity changes as the orientation of the magnetic field at the target position P is changed.

Further, observing E3 in FIG. 9(a), it is understood that when the magnetic field generating units 16a, 16b are rotated while maintaining a full attraction state, the orientation of the magnetic field at the target position P is not changed to the X axial direction or Z axial direction, and the magnetic field intensity does not have an X-axis component or Z-axis component. However, as will be understood from E3 in FIG. 9(b) and FIG. 9(c), the Y-axis component of the magnetic field intensity at the target position P changes under the full attraction state. Specifically, when the magnetic field generating units 16a, 16b are rotated from the state shown in FIG. 7 in the same direction by the same angle, the magnetic field at the target position P keeps its orientation in the plus direction of the Y axis, and decreases gradually in its intensity. Then, as the magnetic field generating units 16a, 16b rotate by 90 degrees, the magnetic field intensity at the target position P becomes almost 0 T. Thereafter, as the magnetic field generating units 16a, 16b are rotated further, the orientation of the magnetic field at the target position P changes from the plus direction to the minus direction of the Y axis, and the magnetic field intensity at the target position P increases gradually.

Figure 10:
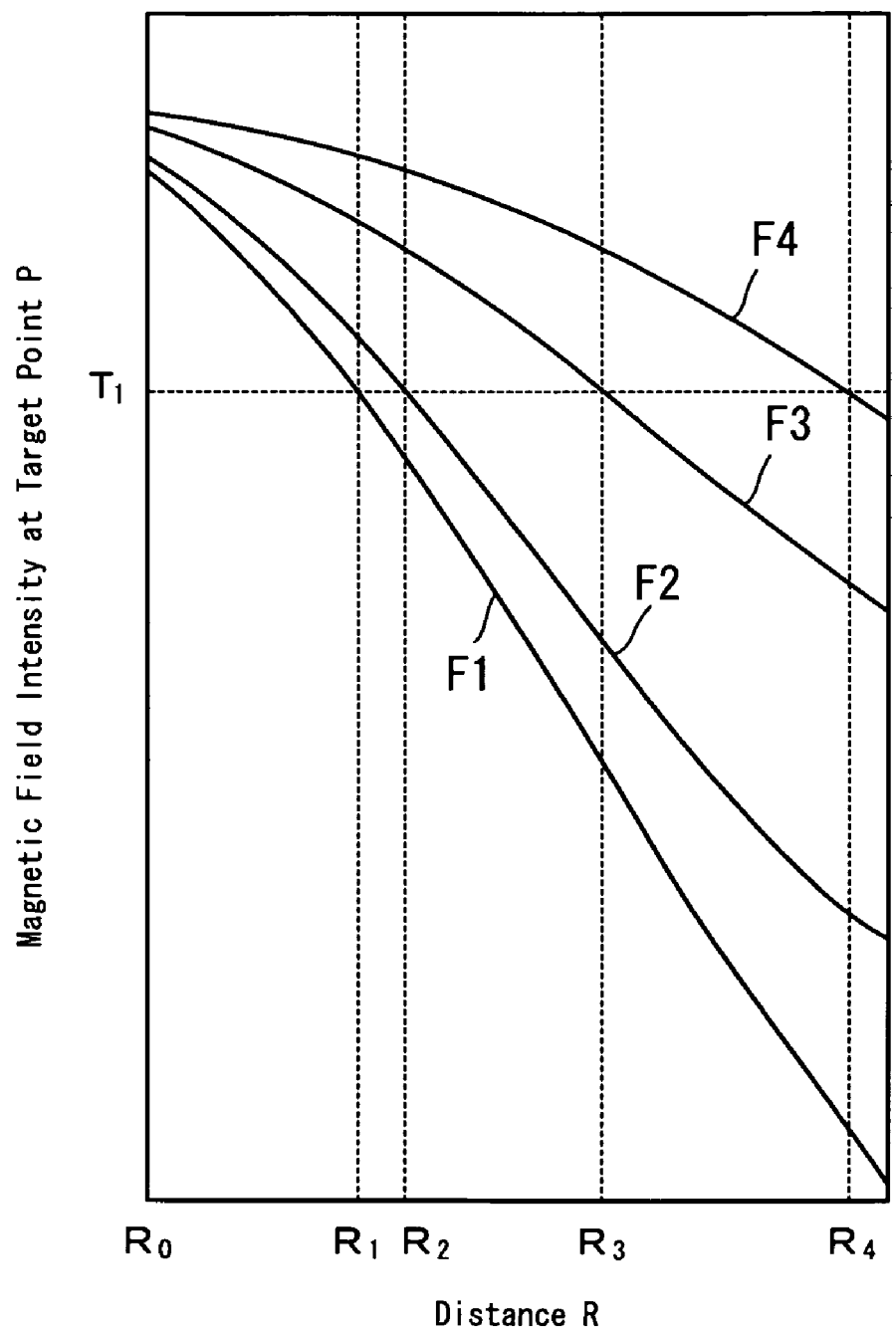
FIG. 10 is a graph which shows a relationship between the magnetic field intensity at a target position and the distance from an intersection made by a rotation axis of the pair of magnetic field generating units and X-axis to the target position.

As described, when the orientation of the magnetic field at the target position P is changed, magnetic field intensity at the target position P also changes. In the magnetic field generator 10, the magnetic field intensity at the target position P is controlled while the orientation of the magnetic field at the target position P is maintained, by changing relative positional relationship between the magnetic field generating units 16a, 16b and the target position P. According to the magnetic field generator 10, an unillustrated actuator moves the magnetic field generating units 16a, 16b in the same direction of directions parallel to the X-Z plane (in the Arrow C directions in this embodiment) by the same distance, thereby controlling the magnetic field intensity at the target position P. FIG. 10 shows a relationship between the distance R from the intersection Q to the target position P and the magnetic field intensity at the target position P.

Referring to FIG. 10, F1 through F4 show changes in the magnetic field intensity at the target position P when the magnetic field generating units 16a, 16b are moved in the same one direction of the Arrow C directions by the same distance, so as to increase the distance R, with the distance R under the state shown in FIG. 5 being $R_0$. Specifically, F1 shows changes in the magnetic field intensity when the magnetic field generating units 16a, 16b under the full repellence state (the state shown in FIG. 5) are moved in an Arrow C direction. F2 shows changes in the magnetic field intensity when the magnetic field generating units 16a, 16b were rotated from the state shown in FIG. 5 in the same one of the Arrow A directions by 30 degrees, and then are moved in an Arrow C direction while maintaining this state. F3 shows changes in the magnetic field intensity when the magnetic field generating units 16a, 16b were rotated from the state shown in FIG. 5 in the same one of the Arrow A directions by 60 degrees, and then are moved in an Arrow C direction while maintaining this state. F4 shows changes in the magnetic field intensity when the magnetic field generating units 16a, 16b were rotated from the state shown in FIG. 5 in the same one of the Arrow A directions by 90 degrees, and then are moved in an Arrow C direction while maintaining this state (the state shown in FIG. 6).

From F1 through F4, it is understood that as the distance R increases, the magnetic field intensity at the target position P decreases. From this, it is understood that the magnetic field intensity at the target position P can be changed arbitrary, by moving the magnetic field generating units 16a, 16b and thereby changing the positional relationship between the target position P and the magnetic field generating units 16a, 16b.

Therefore, it is possible to maintain a constant level of magnetic field intensity at the target position P by changing the distance R in accordance with the orientation of the magnetic field at the target position P. For example, if the magnetic field intensity at the target position P is to be maintained at $T_1$ with the magnetic field generating units 16a, 16b under the state shown in FIG. 5, the distance R should be set to $R_1$ (See F1). Likewise, with the magnetic field generating units 16a, 16b rotated from the state shown in FIG. 5 in the same one direction of the Arrow A directions by 30 degrees, the distance R should be set to $R_2$ (See F2). With the magnetic field generating units 16a, 16b rotated from the state shown in FIG. 5 in the same one direction of the Arrow A directions by 60 degrees, the distance R should be set to $R_3$ (See F3) With the magnetic field generating units 16a, 16b under the state shown in FIG. 6, the distance R should be set to $R_4$ (See F4).

In the magnetic field generator 10, storage means such as a ROM stores data about the predetermined distance R related to a target level of magnetic field intensity to be maintained at the target position P for each orientation of the magnetic field at the target position P. Then, in accordance with a specific orientation of the magnetic field at the target position P, the controller reads data for the distance R from the storage means, and moves the magnetic field generating units 16a, 16b based on the data. With this arrangement, it is possible to maintain the magnetic field intensity at the target position P at a desired level regardless of the orientation of the magnetic field at the target position P.

According to the magnetic field generator 10 as described thus far, it is possible to change the orientation of the magnetic field at the target position P easily and in all directions by combining rotation of the magnetic field generating units 16a, 16b in the same direction by the same angle and rotation of at least one of the magnetic field generating units 16a, 16b. Since the orientation of the magnetic field at the target position P can be changed easily and in all directions by simply rotating the magnetic field generating units 16a, 16b as described, it is possible to make the composition simple and it is easy to control.

By moving the magnetic field generating units 16a, 16b in the same one of the Arrow C directions by the same distance, it is possible to change relative positional relationship between the magnetic field generating units 16a, 16b and the target position P, and thereby to change the magnetic field intensity at the target position P arbitrary. Consequently, it is possible to maintain the magnetic field intensity at the target position P at a constant level. Therefore, in medical instrument systems which guide an object such as a catheter and a capsule endoscope by working of a magnetic field, the magnetic field generator 10 is capable of maintaining the magnetic field intensity which works on the object at a constant level, and therefore can be utilized suitably in such medical systems.

By providing the second main surfaces 30a, 30b of the magnetic field generating units 16a, 16b with magnetic bodies 26a, 26b respectively, it becomes possible to reduce magnetic flux leakage toward the second main surfaces 30a, 30b, and to increase the magnetic field intensity at the target position P.

Since each of the magnetic field generating units 16a, 16b has a circular outer shape, the area where the first main surfaces 28a and 28b oppose to each other does not change when one of the magnetic field generating units 16a, 16b is rotated for example. Because there is no decrease in the area where the first main surfaces 28a and 28b oppose to each other, it is possible to make effective use of the magnetic flux from the magnetic field generating units 16a, 16b.

The first main surface 28a of the magnetic field generating unit 16a is formed with one N pole and one S pole. By making the number of magnetic poles as few as possible as described, it becomes possible to reduce the amount of magnetic flux which makes short cuts to the adjacent unlike pole in the first main surface 28a. The same applies to the magnetic field generating unit 16b. This arrangement allows the magnetic flux to work efficiently at the target position P, and to increase the magnetic field intensity at the target position P.

By composing each of the magnetic field generating units 16a, 16b with a single permanent magnet, the number of parts necessary for building the magnetic field generating units 16a, 16b is reduced and it becomes possible to compose the magnetic field generator 10 more simply.

It should be noted here that in the embodiment given above, description was made for a case where the second main surface 30a of the magnetic field generating unit 16a is provided with a magnetic body 26a, and the second main surface 30b of the magnetic field generating unit 16b is provided with a magnetic body 26b. However, the present invention is not limited to this. The magnetic field generating unit 16b may not be provided with the magnetic body 26b. In other words, only one of the second main surfaces in a pair of magnetic field generating units may be provided with a magnetic body.

Figure 11:
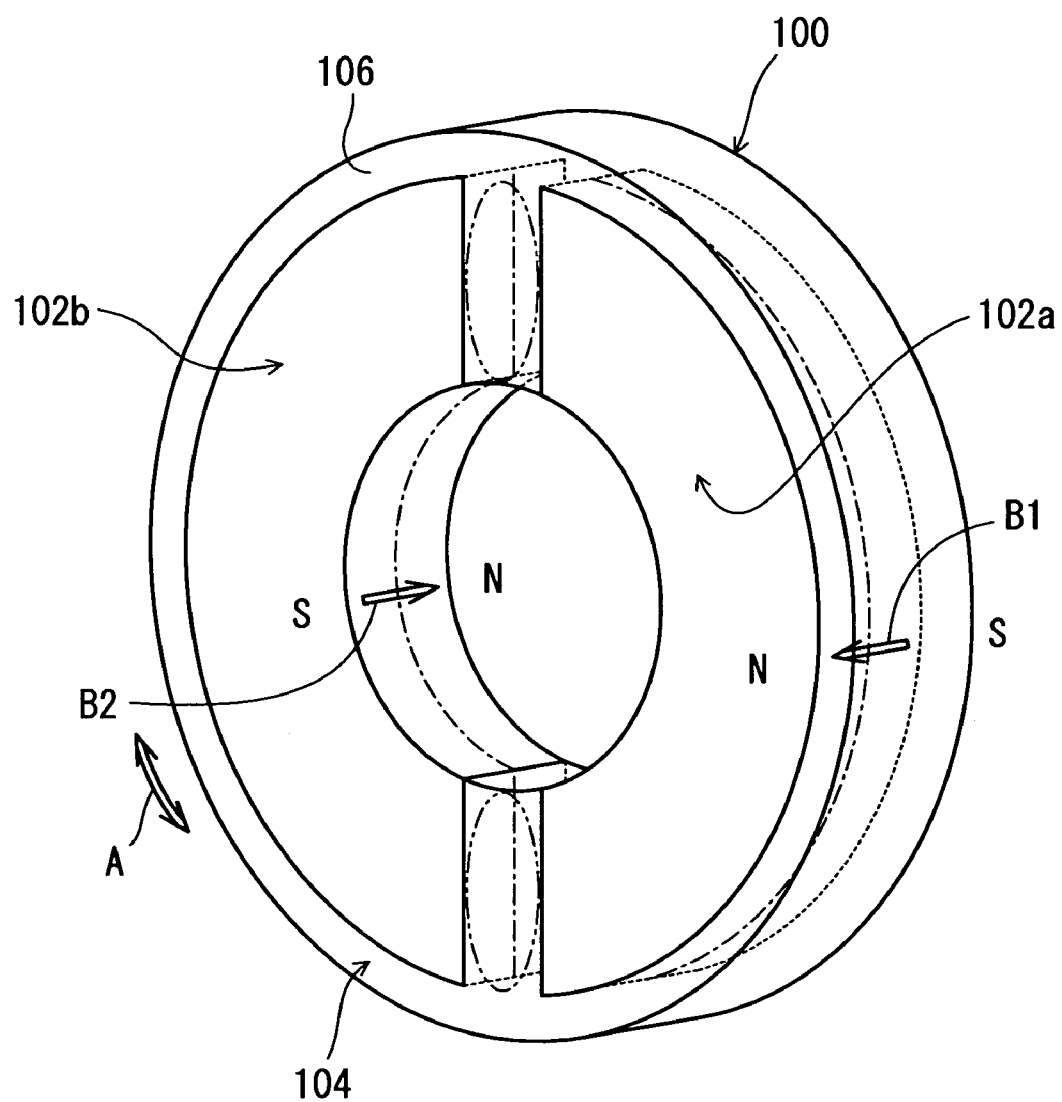
FIG. 11 is a diagram showing a perspective view of another example of the magnetic field generating unit.

It should be noted here that in the embodiment given above, description was made for a case where each of the magnetic field generating units 16a, 16b is made of a single permanent magnet. However, the present invention is not limited to this. For example, a magnetic field generating unit 100 shown in FIG. 11 may be used. The magnetic field generating unit 100 is made of a permanent magnet 102a which is magnetized in an Arrow B1 direction, a permanent magnet 102b which is magnetized in an Arrow B2 direction, and a holding member 104 which holds the permanent magnets 102a, 102b. Each of the permanent magnets 102a, 102b is formed in the shape of a segment so as to be a part of an annular body. The holding member 104 is formed substantially in a ring shape. The permanent magnets 102a, 102b are spaced from each other and fitted into the holding member 104. As described, a magnetic field generating unit 100 can be obtained easily by holding individual permanent magnets 102a, 102b which are magnetized separately from each other, by using the holding member 104. Further, since this makes it possible to dispose the permanent magnets 102a, 102b at a space from each other, it is possible to separate the S pole and the N pole from each other in the first main surface 106. In other words, it is possible to eliminate permanent magnets from near pole-to-pole regions (regions indicated by double-dotted dashed lines) which have virtually no effects on the target position in the first main surface 106 of the magnetic field generating unit 100. Therefore, it becomes possible to reduce the amount of permanent magnet to be used, to reduce the weight of the magnetic field generating units, and to reduce the weight of the magnetic field generator.

In a case where permanent magnets 102a, 102b are fitted into the holding member 104 as in the magnetic field generating unit 100, a closed magnetic circuit will be formed by the permanent magnet 102a, 102b and the holding member 104 if the holding member 104 is a magnetic body. For this reason, it is preferable that the holding member 104 is a nonmagnetic body.

The permanent magnets 102a, 102b may be fixed to a first main surface of a platy (such as disc-shaped) holding member. In this case, it is possible to increase the magnetic field intensity at the target position P by using a magnetic body as a material for the holding member than in a case where a nonmagnetic body is used.

Figure 12:
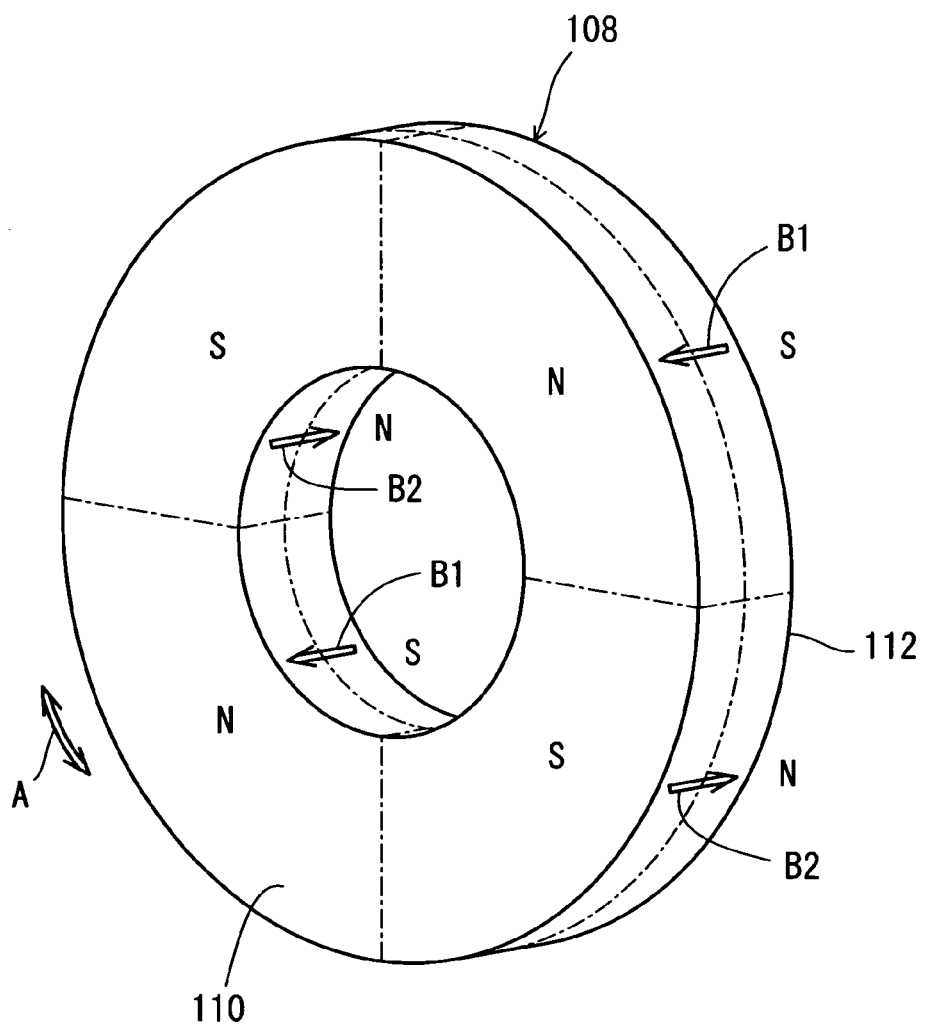
FIG. 12 a diagram showing a perspective view of still another example of the magnetic field generating unit.

In the embodiment given above, description was made for a case where each of the first main surfaces 28a, 28b is formed with two magnetic poles. However, the present invention is not limited to this. For example, a magnetic field generating unit 108 shown in FIG. 12 may be used. The magnetic field generating unit 108 is made of a single permanent magnet. The magnetic field generating unit 108 has a first main surface 110 on which S poles and N poles are alternated with each other in an Arrow A direction, forming four magnetic poles. Further, the magnetic field generating unit 108 has a second main surface 112 where N poles are formed at locations corresponding to the S poles on the first main surface 110, and S poles are formed at locations corresponding to the N poles on the first main surface 110. By using two of the magnetic field generating unit 108 which is of a type called double-surface quad-pole magnetization, it becomes possible to change the orientation of the magnetic field at the target position P on the X-Z plane and to change the inclination of the orientation of the magnetic field at the target position P with respect to the X-Z plane by a half rotation angle as compared to the case where the magnetic field generating units 16a, 16b are used.

Figure 13:
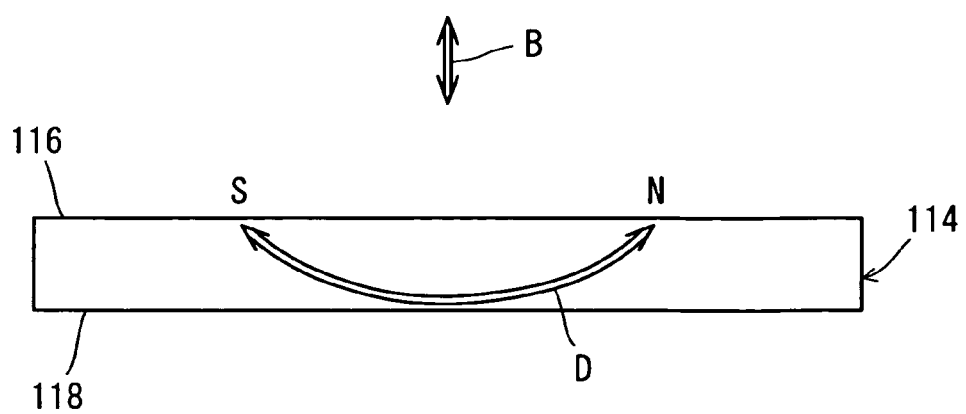
FIG. 13 a diagram showing a perspective view of still another example of the magnetic field generating unit.

Further, in the embodiment given above, description was made for a case where magnetic field generating units 16a, 16b which are magnetized in the Arrow B direction are used. However, the present invention is not limited to this. For example, a magnetic field generating unit 114 shown in FIG. 13 may be used. The magnetic field generating unit 114 is made of a single permanent magnet which is magnetized in a direction extending from a first main surface 116 toward a second main surface 118 and then returning to the first main surface 116 (Arrow D direction). In the magnetic field generating unit 114 provided by a so called polar-anisotropic permanent magnet as described, magnetic poles are formed only on the first main surface 116. In the magnetic field generating unit 114 of such a composition, a large amount of magnetic flux is obtained from the first main surface 116, which enables to increase the magnetic field intensity at a target position.

It should be noted here that in the embodiment given above, description was made for a case where magnetic field generating units 16a, 16b are disposed on the right side and left side. However, the present invention is not limited to this. For example, a pair of magnetic field generating units may be opposed in an up-down direction.

Further, in the embodiment given above, description was made for a case where magnetic field intensity at a predetermined target position P is changed by moving the magnetic field generating units 16a, 16b. However, the present invention is not limited to this. For example, the magnetic field intensity at the target position may be changed by moving the target position with respect to the pair of magnetic field generating units while maintaining the orientation of the magnetic field at the target position. In this case, the magnetic field intensity at the target position can be maintained at a constant level by controlling the location to which the target is moved and the distance of the movement. Specifically, if a magnetic field generator 10 is to be used in the above-described medical system, the patient may be moved while maintaining the orientation of the magnetic field at a certain position (target position) inside the patient's body, whereby a change is made for the relative positional relationship between the magnetic field generating units 16*a*, 16*b* and the target position inside the patient. With this arrangement, it is possible to change the magnetic field intensity at a target position inside the patient. In this case, it is possible to maintain the magnetic field intensity at the target position inside the patient at a constant level by controlling the position where the patient is moved and the distance of the movement.

Further, in the embodiment given above, description was made for a case where the rotation drive units 20*a*, 20*b* are driven by motors which are controlled by a controller that defines the control means. However, the present invention is not limited to this. For example, the rotating means may rotate the rotation member as a handle is rotated. In other words, the rotating means may be driven and controlled manually.

Further, in the embodiment given above, description was made for a case where the sliders 34*a*, 34*b* are moved by actuators which are controlled by a controller that defines control means. However, the present invention is not limited to this. For example, the moving means may move the slider as a handle is rotated. In other words, the moving means may be driven and controlled manually.

It should be noted here that there is no specific limitation to the outer shape of the first main surface of the magnetic field generating unit. The magnetic field generating units may have a first main surface whose outer shape is polygonal.

Also, the first main surface in one of the magnetic field generating units may have a different outer shape from the outer shape of the other first main surface of the other magnetic field generating unit in the pair, or the two first main surfaces may be different in size. For example, a magnetic field generating unit whose first main surface has a circular outer shape and a magnetic field generating unit whose first main surface has a triangular outer shape may be used.

Also, a pair of magnetic field generating units may be provided by a magnetic field generating unit whose first main surface is formed with two magnetic poles (such as the magnetic field generating units 16*a*, 100, 114) and another magnetic field generating unit whose first main surface is formed with three or more magnetic poles (such as the magnetic field generating unit 108).

Also, a pair of magnetic field generating units may be provided by a magnetic field generating unit which is made of a single permanent magnet (such as the magnetic field generating units 16*a*, 108, 114) and another magnetic field generating unit which is made of a plurality of permanent magnets held by a holding member (such as the magnetic field generating unit 100).

Also, in a case where a permanent magnet for use in the magnetic field generating unit is large and it is difficult to provide the permanent magnet by a single piece of permanent magnet, the permanent magnet may be provided by a plurality of permanent magnet pieces (magnet blocks) assembled integrally with each other.

Also, an electric magnet, etc. may be used instead of a permanent magnet as a magnetic field generating source of the magnetic field generating unit.

Also, a pair of magnetic field generating units may be rotated only in the same direction and by the same angle, or only one of the magnetic field generation units in the pair may be rotated. In other words, only the step of changing the orientation of the magnetic field at a target position on a predetermined plane may be performed, or only the step of changing the inclination of the orientation of the magnetic field at a target position with respect to the predetermined plane may be performed.

Further, the step of changing the orientation of the magnetic field at a target position on the predetermined plane may be performed simultaneously with the step of changing the inclination of the orientation of the magnetic field at a target position with respect to the predetermined plane. Specifically, for example, the pair of magnetic field generating units may be rotated in the same direction by different angles (at different speeds), or the pair of magnetic field generating units may be rotated in mutually reverse directions from each other by different angles. As described, any mode of driving the pair of magnetic field generating units may be used as long as the magnetic field is set in a desired orientation at the target position. Also, a change in the orientation of the magnetic field at a target position may be performed simultaneously with a change in the magnetic field intensity at a target position. Specifically, for example, rotation and movement of the pair of magnetic field generating units may be performed simultaneously.

The present invention being thus far described and illustrated in detail, it is obvious that these description and drawings only represent examples of the present invention, and should not be interpreted as limiting the invention. The spirit and scope of the present invention is only limited by words used in the accompanied claims.

The invention claimed is:

1. A magnetic field control method using a pair of coaxially disposed magnetic field generating units each having a first main surface opposed in parallel to the other with a gap and formed with a plurality of magnetic poles, for controlling a magnetic field generated by the pair of magnetic field generating units, sandwiched by the pair of magnetic field generating units and being at a target position on a predetermined plane which is in parallel to the first main surface, the method comprising:

a step of changing an orientation of the magnetic field at the target position on the predetermined plane by rotating each of the magnetic field generating units in a same one direction of circumferential directions by a same angle, and a step of changing an inclination of the orientation of the magnetic field at the target position with respect to the predetermined plane by at least rotating one of the magnetic field generation units and rotating another one of the magnetic field generation units in the pair in a circumferential direction so as to change a positional relationship between the magnetic pole in one of the magnetic field generating units and the magnetic pole in the other of the magnetic field generating units, wherein one of the magnetic field generation units is rotated by a first rotation drive unit, another one of the magnetic field generation units being rotated by a second rotation drive unit, and the first and the second rotation drive units being driven separately from each other.

2. The magnetic field control method according to claim 1, further comprising a step of changing an intensity of the magnetic field at the target position while maintaining the orientation of the magnetic field at the target position, by changing a relative positional relationship between the pair of magnetic field generating units and the target position.

3. A magnetic field generator comprising: a pair of coaxially disposed magnetic field generating units each having a first main surface opposed in parallel to the other with a gap and formed with a plurality of magnetic poles; and a first rotation drive unit for rotating one of the magnetic field generating units and a second rotation drive unit for rotating another one of the magnetic field generating units in the pair in a circumferential direction for changing an orientation of a magnetic field generated by the pair of magnetic field generating units, sandwiched by the pair of magnetic field generating units and being at a target position on a predetermined plane which is in parallel to the first main surface, the first and the second rotation drive units being driven separately from each other.

4. The magnetic field generator according to claim 3, further comprising moving means for moving each of the magnetic field generating units in the pair in a direction which is parallel to the predetermined plane, by a same distance for changing the magnetic field intensity at the target position.

5. The magnetic field generator according to claim 3 or 4, wherein at least one of the magnetic field generating units has a second main surface facing away from the first main surface, the magnetic field generator further comprising a magnetic body provided in the second main surface.

6. The magnetic field generator according to claim 3 or 4, wherein the first main surface in at least one of the magnetic field generating units has a circular outer shape.

7. The magnetic field generator according to claim 3 or 4, wherein the first main surface in at least one of the magnetic field generating units is formed with two of the magnetic poles.

8. The magnetic field generator according to claim 3 or 4, wherein at least one of the magnetic field generating units is provided by a single permanent magnet.

9. The magnetic field generator according to claim 3 or 4, wherein at least one of the magnetic field generating units is constituted by a plurality of permanent magnets and a holding member holding the permanent magnets.

* * * * *